United States Patent [19]

Mezei et al.

[11] Patent Number: 5,473,072
[45] Date of Patent: Dec. 5, 1995

[54] PROCESS FOR THE PREPARATION OF HIGH PURITY BUSPIRON AND THE HYDROCHLORIDE THEREOF

[75] Inventors: Tibor Mezei; Gábor Blaskó; Zoltán Budai; Margit Csörgö; Éva Furdyga; Imre Klebovich, all of Budapest; László Koncz, Magyoród; Ilona Sztruhár, Budapest; Attila Mándi; Kálmán Nagy, Budapest; Klára Reiter née Esses, Budapest; Gyula Simig, Budapest; Judit Szegö, Budapest; Gyöngyi Vereczkey née Donáth, Budapest, all of Hungary

[73] Assignee: Egis Gyogyszergyar Rt., Budapest, Hungary

[21] Appl. No.: 274,848

[22] Filed: Jul. 14, 1994

[30] Foreign Application Priority Data

Jul. 16, 1993 [HU] Hungary .................... P9302040

[51] Int. Cl.⁶ .................... C07D 403/04
[52] U.S. Cl. .................... 544/295
[58] Field of Search .................... 544/295

[56] References Cited

U.S. PATENT DOCUMENTS 5,334,715  8/1994  Ong et al. .................... 544/392

OTHER PUBLICATIONS

Kojima et al., Chemical Abstracts, 110(3):23,914e, 1989, abstract of JP 6310760 (18 Jan. 1988).
Kuo et al., Chemical Abstracts, 120(13):164,231y, abstract of CH 682,563 (15 Oct. 1993).
Kuo et al, Heterocycles, 36(7), 1463–1469, (1993).
Budai et al, Chemical Abstracts 110(5):39,018b, abstract of DE 3,806,009 (25 Feb. 1987).

*Primary Examiner*—Mukund J. Shah
*Assistant Examiner*—Matthew V. Grumbling
*Attorney, Agent, or Firm*—Beveridge, DeGrandi, Weilacher & Young

[57] ABSTRACT

Process for the preparation of 8-[4-[4-(pyrimidine-2-yl)-piperazine-1-yl]-butyl]-8-aza-spiro[4.5]decane-7,9-dione (buspiron) of the Formula I

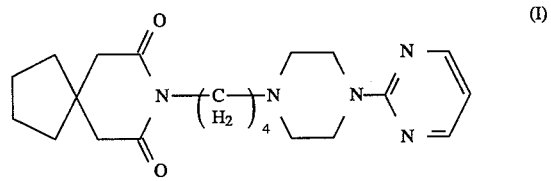

and the hydrochlorides thereof having high purity by continuously adding a solution of 8-[4-[4-(pyrimidine-2-yl)-piperazine-1-yl]-but-2-inyl]-8-aza-spiro[4.5]decane-7,9-dione of the formula II

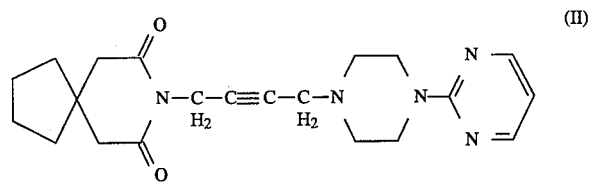

formed with an inert organic solvent having a concentration of at least 40% by weight to a suspension of a hydrogenation catalyst in an inert organic solvent and optionally converting the 8-[4-[4-(pyrimidine-2-yl)-piperazine-1-yl]-butyl]-8-aza-spiro[4.5]decane-7,9-dione thus obtained into the hydrochloride thereof.

16 Claims, No Drawings

PROCESS FOR THE PREPARATION OF HIGH PURITY BUSPIRON AND THE HYDROCHLORIDE THEREOF

This invention relates to a new and improved process for the preparation of 8-[4-[4-(pyrimidine-2-yl)-piperazine--1-yl]-butyl]-8-aza-spiro[4.5]decane-7,9-dione (Buspiron) and the hydrochloride thereof having high purity and free of by-products.

The compound 8-[4-[4-(pyrimidine-2-yl)-piperazine-1-yl]-butyl]-8-aza-spiro[4.5]decane-7,9-dione of the Formula I

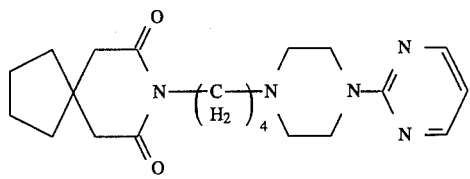

is a known and valuable anxioselective active ingredient (GB-PS 1,332,194).

Several procedures are known for the preparation of this compound.

According to GB-PS 1,332,194 the compound of the Formula I is prepared by reacting 8-oxa-spiro[4.5]decane-7,9-dione with 1-]4-aminobutyl]-4-[pyrimidine-2-yl]-piperazine. The reaction is carried out in pyridine at the boiling point of the reaction mixture.

The desired compound of the Formula I is obtained in the form of a crude product with moderate yields. The crude product is purified in the form of the free base either by crystallization or by fractionated distillation in vacuo. The disadvantage of the first mentioned purification method is that high losses occur. The fractionated distillation is performed at a high temperature (240°–265° C.) at a low pressure (13.3 Pa) and for this reason the product is subjected to a serious thermal load which leads to decomposition.

According to an other process disclosed in GB-PS 1,332, 194 8-(4-chlorobutyl)-8-aza-spiro[4.5]-decane-7,9dione is reacted with N-(pyrimidine-2-yl)-piperazine in the presence of sodium carbonate in n-butanol at the boiling point of the reaction mixture. The reaction time is 3 days. Because of the extremely long reaction time the process is unsuitable for industrial scale production. A further drawback of the process is that the purification of the product is very complicated, expensive and requires operations which are to be carried out with big care. A still further disadvantage of this process resides in the fact that the 1-bromo-4-chloro-butane used by the preparation of the starting material 8-(4-chlorobutyl)-8-aza-spiro[4,5]-decane-7,9-dione is a very difficult available compound and the preparation thereof encounters serious difficulties.

According to a still further process disclosed in GB-PS 1,322,194 in the first step 1-(4-chlorobutyl)-4-(2-pyrimidinyl)-piperazine prepared from 1-bromo-4-chloro-butane is reacted with 8-aza-spiro[4.5]decane. This synthesis route contains however numerous sensitive steps which can be carried out with substantial difficulties. The desired end-product of the Formula I can be prepared in a purity suitable for pharmaceutical use only by subjecting the crude product to numerous purification steps. A further disadvantage resides in the difficult availability of the 1-bromo-4-chloro-butane used as starting material.

The 1-(4-aminobutyl)-4-(pyrimidine-2-yl)-piperazine can be prepared by heating 1-(pyrimidine-2-yl)-piperazine with 3-chloro-propionitrile in n-butanol as reaction medium for a longer period of time (about 16 hours). The intermediate thus obtained must be purified by crystallization (yield 70%). The intermediate nitrile compound is subjected to catalytic hydrogenation which can be carried out with a yield of about 70% (GB-PS 1,332,194).

A further process for the preparation of the compound of the Formula I is set forth in HU-PS No. 187,999. The 1-(4-chlorobutyl)-4-(pyrimidine-2-yl)-piperazine is converted into a spiro-quaternary ammonium-piperazine derivative of the general formula III

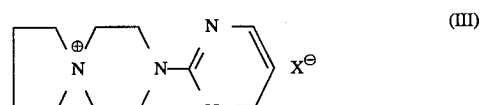

(wherein X– is a halide anion) whereupon the product thus obtained is reacted with 8aza-spiro[4.5]decane-7,9-dione in the presence of a strong base. This process is, however, accompanied by serious disadvantages. The yield is low, the synthesis route consists of a number of steps and the purification of the product encounters difficulties. For these reasons the process cannot be used for industrial scale production.

According to CH-PS No. 647,518 8-aza-spiro[4,5]decane-7,9-dione is first reacted with 1,4-dibromo-butane, whereupon the 4-bromobutyl derivative thus obtained is reacted with piperazine and the product thus obtained is treated with 2-chloro-pyrimidine. The The purpose of this process is to prepare a $^{14}$C-isotope marked compound and the process is suitable only for laboratory scale preparation but not for industrial scale manufacture.

According to ES-PS No. 536,286 the potassium salt of 8-aza-spiro[4.5]decane-7,9-dione is reacted with 4-chloro-butyraldehyde, whereupon the product thus obtained is reacted with N-(pyrimidine-2-yl)-piperazine under reducing conditions. This process is, however, only of theoretical significance and plays no role in industrial scale production.

The object of DE-OS 3,806,009 is to eliminate the above drawbacks of the known processes. The essence of the process described in the cited DOS is to convert the unsaturated compound 8-[4-[4-(pyrimidine- 2-yl)-piperazine-1-yl]but-2-inyl]-8-aza-spiro[4.5]decane-7,9-dione by catalytic hydrogenation into the desired compound 8-[4-[4-(pyrimidine-2-yl)-piperazine-1-yl]-butyl-8-aza-spiro[4.5]decane-7, 9-dione.

Catalytic hydrogenation is carried out in the presence of a metal catalyst, particularly palladium, preferably used on a support (e.g. coal) in an organic solvent. Aliphatic alcohols are used as reaction medium. The melting point of the product thus obtained amounts to 91°–99° C.

The extremely rapid development of the analytical equipments and methods used for the determination of purity and the higher and higher analytical requirements raised by pharmaceutical industry make the use of active ingredients of an increasingly higher purity for the preparation of pharmaceutical products (medicines) a highly important necessity.

According to the prescriptions of the Pharmacopoeia the upper limit of the total amount of all impurities present amounts generally to 0.5% by weight, whereby the amount of the unidentified contaminations should not exceed the value of 0.1% by weight.

According to our experiments the process disclosed in DE-OS 3,806,009 is unable to provide a compound 8-[4-[4-(pyrimidine-2yl)piperazine-1-yl]-butyl]-8-aza-spiro[4.5]

decane-7,9-dione of highest purity. The product thus obtained contains numerous contaminations. The determination of the structure of such impurities shows that these substances are either derived from the incomplete catalytic hydrogenation of the compound of the Formula II and thus contaminate the end product of the Formula I or are formed after hydrogenation. The structure of the latter impurities was determined by GC/MS methods and found to be 1-(pyrimidine-2-yl)-piperazine and 8-aza-spiro[4.5]decane-8-butyl-7,9-dione. The formation of these impurities can be readily explained on the basis of the article of G. F. Hennion and G. A. Ferrino [J.Org.Chem. 26, 1073 (1961)]. According to this article the C-N bond can be split after the partial saturation of the triple bond.

It is known that the hydrochloride salt of 8-[4-[4-(pyrimidine-1-yl]-piperazine-1-yl]-butyl]-8-aza-spiro[4.5]decane-7,9-dione crystallizes in different crystalline forms and the different polymorphs may be converted into each other. One of the polymorphs has a melting point of 188°–191° C. (referred to as P 188), while the other has a melting point of 201°–203° C. (referred to as P 203). This product is disclosed in U.S. Pat. No. 4,810,789. Both polymorphs are characterized by the melting point, determined by DSC (Differential Scanning Calorimetry) methods.

It is also known that the IR-spectrum of the different polymorphs shows minor differences [M. Kuhnert-Brandstätter, U. Porsche: Scientia Pharmaceutica 58, 37–53 (1990)]. The polymorph P 188 shows an absorption at 1290 cm$^-$, while the polymorph P 203 shows an absorption at 1150 cm$^{-1}$. The presence or absence of the characteristic absorption indicates the presence of one polymorph or the other, while from the ratio of the intensities conclusions can be drawn as to the ratio of the polymorphs.

According to EP-OS 304 940 A1 the P 203 polymorph of Buspiron hydrochloride is prepared by disrupting the crystalline structure of the P 188 polymorph or a mixture of the P 188 and P 203 polymorphs by partial or complete dissolving, crystallizing the compound at a temperature above 95° C. and separating the precipitated crystals. As solvent preferably butanol, cyclohexanone, nonane, xylene or mixtures thereof can be used. According to EP-OS 304,941 A1 the P 188 polymorph of Buspiron hydrochloride is prepared by disrupting the crystalline structure of the P 203 polymorph of buspiron hydrochloride by partial or complete dissolving, crystallizing the compound at a temperature below 95° C. and separating the precipitated crystals.

According to the disclosure of EP-OS 304,940 A1 and 304 941 A1 the temperature limit of 95° C. plays a decisive role. Thus at a temperature below 95° C. the crystallization of the P 188 polymorph takes place, while at a temperature above 95° C. the P 203 polymorph of buspiron hydrochloride crystallizes. The above cited two EP-OS are silent in disclosing in a detailed manner the chemical synthesis by which the buspiron base of the Formula A was prepared.

It is the object of the present invention to overcome the disadvantages of the known methods, particularly those of the process disclosed in DE-OS 3,806,009.

It is a further object of the present invention to provide a process which enables the preparation of highly pure hydrochlorides of the compound 8-[4-[4-(pyrimidine-2-yl)-piperazine-1-yl]-butyl-8-aza-spiro[4.5]decane-7,9-dione meeting the standards of pharmacopoeia with good yields without any subsequent purification.

The above objects are achieved by the present invention in an unaforeseen manner.

The present invention is based on the surprising recognition that when the hydrogenation of the compound of the Formula II

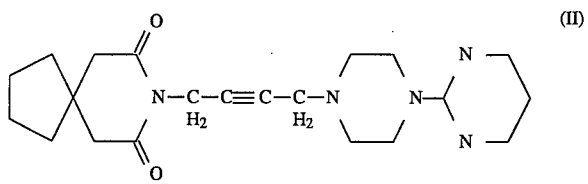

is carried out by adding a solution of the compound of the Formula II formed with an inert organic solvent to a suspension of the catalyst in an inert organic solvent a highly pure compound of the Formula I is obtained which contains less than 0.1% by weight of contaminations (according to HPLC analysis). It has been found, on the other hand, that the change of the temperature (between 20° C. and 60° C.) and the pressure (between 1 and 8 bar) do not exert any substantial effect on the purity of the product and the yield.

According to the present invention there is provided a process for the preparation of 8-[4-[4-(pyrimidine-2-yl)-piperazine-1-yl]-butyl]-8-aza-spiro[4.5]decane-7,9-dione (Buspiron) of the Formula I and the hydrochlorides thereof having high purity by subjecting 8-[4-[4-(pyrimidine-2-yl)-piperazine-1-yl]-but-2-inyl]-8-aza-spiro[4.5]decane-7,9-dione of the Formula II to catalytic hydrogenation in the presence of a palladium or Raney-nickel catalyst in an inert organic solvent and optionally converting the 8-[4-[4-(pyrimidine-2-yl)-piperazine-1-yl]-butyl]-8-aza-spiro[4.5]decane-7,9-dione thus obtained into the hydrochloride thereof which comprises continuously adding a solution of 8-[4-[4-(pyrimidine-2-yl)-piperazine-1-yl]-but-2-inyl]-8-aza-spiro[4.5]-decane-7,9-dione formed with an inert organic solvent having a concentration of at least 40% by weight to a suspension of a catalyst in an inert organic solvent, removing the catalyst and subsequently a) isolating the 8-[4-[4-(pyrimidine-2-yl)-piperazine-1-yl]-butyl]-8-aza-spiro[4.5]decane-7,9-dione base and/or b) treating the 8-[4-[4-(pyrimidine-2-yl)-piperazine-1-yl]-butyl]-8-aza-spiro[4.5]decane-7,9-dione base with hydrogen chloride in ethanol or isopropanol under stirring at a temperature between 15° C. and 40° C. and isolating the 8-[4-[4-(pyrimidine-2-yl)-piperazine-1-yl]-butyl]-8-aza-spiro[4.5]decane-7,9-dione hydrochloride melting at 188°–191° C., or c) treating the 8-[4-[4-(pyrimidine-2-yl)-piperazine-1-yl]-butyl]-8-aza-spiro[4.5]decane-7,9-dione base with hydrogen chloride in ethyl acetate or isopropanol at a temperature not exceeding 70° C. under stirring and isolating the 8-[4-[4-(pyrimidine-2-yl)-piperazine-1-yl]-butyl]-8-aza-spiro[4.5]decane-7,9-dione hydrochloride melting at 201°–203° C.

It is preferred to use a solution of the compound of the Formel II having a concentration between 40 and 70% by weight.

According to a preferred embodiment of the process of the present invention the solution of the compound of the Formula II is formed with a polar protic solvent and/or an apolar aprotic solvent snad/or a polar aprotic solvent.

According to a particularly preferred embodiment of the process of the present invention methanol and/or ethanol (polar protic solvent), benzene (apolar aprotic solvent) and/or tetrahydrofurane (polar aprotic solvent) is used as solvent for the starting material of the Formula II. As inert organic solvent for suspending the palladium or Raney-nickel catalyst preferably methanol, ethanol, benzene and/or tetrahydrofurane may be used.

It is preferred to use a palladium catalyst applied onto a support, particularly carbon.

According to a particularly preferable embodiment of the process of the present invention the same solvent is used for dissolving the starting material of the Formula II as used for suspending the catalyst.

According to a further particularly preferred embodiment of the process of the present invention the solution of the starting material of the Formula II is added continuously to the suspension of the catalyst at such a rate that the weight ratio of the compound of the Formula II and the catalyst amounts to (0.01–1): 1.

The hydrogenation is advantageously carried out at a temperature between 10° C. and 50° C., preferably at 20°–30° C.

The hydrogenation can be advantageously performed under a pressure of 1–10 bar, preferably under 1–5 bar.

The reaction mixture can be worked up according to several methods.

According to one form of realization of the process of the present invention the base of the Formula I is isolated (process a). This process can be carried out by filtration or centrifugation and subsequent evaporation of the filtrate. A highly pure compound of the Formula I containing not more than 0.1% of impurities can be directly obtained without further crystallization or recrystallization.

According to an other form of realization of the process of the present invention (process b) the base of the Formula I is treated with hydrogen chloride at a temperature between 15° C. and 40° C. in ethanol or isopropanol and 8-[4-[4-(pyrimidine-2-yl)-piperazine-1-yl]-butyl]-8-aza-spiro/4.5/decane-7,9-dione hydrochloride melting at 188°–191° C. is isolated. The reaction is preferably carried out at a temperature of about 20° C.

According to a still further form of realization of the process of the present invention (process c) the base of the Formula I is treated with hydrogen chloride at a temperature not exceeding 70° C. in ethyl acetate or isopropanol and 8-[4-[4-(pyrimidine-2yl)-piperazine-1-yl]-butyl]-8-aza-spiro/4.5/decane-7,9-dione hydrochloride melting at 201°–203° C. is isolated. The reaction is carried out preferably at a temperature between 40° C. and 65° C., particularly at a temperature of about 60° C.

One may proceed preferably by using the base of the Formula I for salt formation in the form of the solution containing this compound obtained after removing the catalyst.

The addition of hydrogen chloride in ethanol or isopropanol or ethyl acetate, respectively, to the base of the Formula I may be preferably performed for a period of 5–30 minutes.

Stirring promotes the crystallization of 8-[4-[4-(pyrimidine-2-yl)-piperazine-1-yl]-butyl]-8-aza-spiro[4.5]decane-7,9-dione hydrochloride and for this reason salt formation is preferably carried out under stirring.

The base of the Formula I is treated with hydrogen chloride in ethanol or isopropanol or ethyl acetate, respectively, under stirring to yield 8-[4-[4-(pyrimidine-2-yl)-piperazine-1-yl]-butyl]-8-aza-spiro[4.5]decane-7,9-dione hydrochloride for a period of 1–5 hours.

The process of the present invention has several advantages over the methods described in prior art which can be summarized as follows:

a) The yields are higher than by the known processes.
b) Highly pure base of the Formula I is obtained which contains only a minimal amount of impurities.
c) The base of the Formula I obtained can be used for the preparation of 8-[4-[4-(pyrimidine-2-yl)-piperazine-1-yl]-butyl]-8-aza-spiro[4.5]decane-7,9-dione hydrochloride polymorphs of different crystalline structure directly without further purification.

Further details of the present invention are to be found in the following Examples which serve only to illustrate the process but do not limit the scope of protection. The melting points were measured in a capillary in the conventional manner and the 8-[4-[4-(pyrimidine-2-yl)-piperazine-1-yl]-butyl]-8-aza-spiro[4.5]decane-7,9-dione base was determined by titration in anhydrous medium with perchloric acid.

EXAMPLE 1

Preparation of
8-[4-[4-(pyrimidine-2-yl)-piperazine-1-yl]-butyl]-8-aza-spiro[4.5]decane-7,9-dione A solution of 100 g (0.26 mole) of 8-[4-[4-(pyrimidine-2-yl)-piperazine-1-yl]-but-2-inyl]-8-aza-spiro[4.5]-decane-7,9-dione in 140 ml methanol is added to a suspension of 4 g of a palladium/carbon catalyst (palladium content about 5% by weight) and 250 ml of methanol under vigorous stirring under introduction of hydrogen at a pressure of 1 bar at such a rate that the hydrogen uptake of the unsaturated compound 8-[4-[4-(pyrimidine-2-yl)-piperazine-1-yl]-but-2-inyl]-8-aza-spiro[4.5]decane-7,9-dione added is substantially identical with the calculated hydrogen consumption (this is continuously measured by means of a gas burette). This means in the practice that when the addition of the starting material is stopped, the hydrogen consumption ceases within 5–10 seconds. The addition of the solution of 8-[4-[4-(pyrimidine-2-yl)-piperazine-1-yl]-but-2-inyl]-8-aza-spiro[4.5]decane-7,9-dione takes 2–4 hours, depending on the rate of stirring and the temperature (20°–30° C.).

After termination of hydrogenation the catalyst is filtered off. The catalyst can be used for the next hydrogenation operation without any further treatment. The filtrate is evaporated, the residue is suspended in isopropanol and filtered. Thus in form of white crystals 100.3 g of 8-[4-[4-(pyrimidine-2-yl)-piperazine-1-yl]-butyl]-8-aza-spiro[4.5]decane-7,9-dione base are obtained. Yield: about 100%. Mp.: 105°–106° C. (according to prior art 90°–98° C.). Content (on the base): 99.8–100.1%. According to HPLC analysis the product contains only about 0.1% of contaminations.

Example 2

Preparation of
8-[4-[4-(pyrimidine-2-yl)-piperazine-1-yl]-butyl]-8-aza-spiro[4.5]decane-7,9-dione hydrochloride A solution of 100 g (0.26 mole) of 8-[4-[4-(pyrimidine-2-yl)-piperazine-1-yl]-but-2-inyl]-8-aza-spiro[4.5]decane-7,9-dione in 140 ml ethanol is added to a suspension of 0.5 g of a palladium/carbon catalyst (palladium content about 5% by weight) and 300 ml of ethanol at room temperature under introduction of hydrogen under a pressure of 5 bar. When the addition of the starting material is stopped, the hydrogen consumption ceases immediately. The catalyst is filtered off at a temperature of 60° C. The catalyst can be directly used in the next hydrogenation operations without any further treatment.

a) To the solution thus obtained 50 ml of ethanol, containing 9.5 g (0.26 mole) of hydrogen chloride, are added within 5–10 minutes at a temperature of 20° C. This temperature is maintained by cooling, if necessary. The reaction mixture is stirred for one hour and a half whereupon the precipitated product is filtered and dried. Thus in the form of white crystals 107.8 g of 8-[4-[4-(pyrimidine-2-yl)-piperazine-1-yl]-butyl]-8-aza-spiro[4.5]decane-7,9-dione-hydrochloride are obtained, yield 97.5%. Mp.: 188°–189° C. DSC/10° C./Min 190° C. Content (obtained by determining the base content): 99.9%. According to HPLC analysis the product contains less than 0.1% of contaminations.

At 1150 $cm^{-1}$ the IR spectrum of the product shows no peak characteristic of the polymorph melting at 201°–203° C.

b) From the solution of 8-[4-[4-(pyrimidine-2-yl)-piperazine-1yl]-butyl]-8-aza-spiro[4.5]decane-7,9-dione base obtained according to the first paragraph of this Example the catalyst is filtered off, whereupon the solvent is replaced by 1000 ml of isopropanol. To the suspension formed 50 ml isopropanol containing 9.5 g (0.26 mole) of hydrogen chloride are added at 20° C. within 15 minutes. The temperature is kept at the above value by cooling, if necessary.

Stirring is continued for a further period of one hour and a half, whereupon the precipitated product is filtered off and dried. Thus in the form of white crystals 106.2 g of 8-[4-[4-(pyrimidine-2-yl)-piperazine-1-yl]-butyl]-8-aza-spiro[4.5]decane-7,9-dione hydrochloride are obtained, yield 96.8 %. The product is identical (melting point, purity) with the substance obtained by using ethanol (see par. a).

c) From the solution of 8-[4-[4-(pyrimidine-2-yl)-piperazine-1-yl]-butyl]-8-aza-spiro[4.5]decane-7,9-dione base obtained according to the first paragraph of this Example the catalyst is filtered off, whereupon the solvent is replaced by 500 ml of ethyl acetate. To the suspension formed ethyl acetate containing 9.5 g (0.26 mole) of hydrogen chloride is added within 10 minutes at 60° C. The reaction mixture is stirred for an hour and a half, the precipitated product is filtered off and dried. Thus 94 g of 8-[4-[4-(pyrimidine-2-yl)-piperazine-1-yl]-butyl]-8-aza-spiro[4.5]decane-7,9-dione-hydrochloride are obtained in the form of white crystals. Yield 85%. Melting point: 203°–204° C. DSC/20° C./Min.= 206.59° C. According to HPLC analysis the product contains less than 0.1% of contaminations. content (obtained by determining the base content): 99.5–100.5%. At 1290 $cm^{-1}$ the IR spectrum of the product shows no peak characteristic of the polymorph melting at 188°–191° C.

d) One proceeds as described in Par. c) except that ethyl acetate is replaced by isopropanol. Thus 86.4 g of 8-[4-[4-(pyrimidine-2-yl)-piperazine-1-yl]-butyl]-8-aza-spiro[4.5]decane-7,9-dione-hydrochloride are obtained. M.p.: 203°–204° C.

The purity of the product is identical with that of 8-[4-[4-(pyrimidine-2-yl)-piperazine-1-yl]-butyl-8aza-spiro[4.5]decane-7,9-dione-hydrochloride obtained according to Par. c).

EXAMPLE 3

Preparation of
8-[4-[4-(pyrimidine-2-yl)-piperazine-1-yl]-butyl]-8-aza-spiro[4.5]decane-7,9-dione A solution of 100 g (0.26 mole) of 8-[4-[4-pyrimidine-2-yl)-piperazine-1-yl]-but-2-inyl]-8-aza-spiro[4.5]decane-7,9-dione in 140 ml of methanol is added to a suspension of 8 g of Raney-nickel and 250 ml of methanol at a temperature of 20°–40° C. and under a pressure of 5 bar at such a rate that the hydrogen uptake of the unsaturated compound 8-[4-[4-(pyrimidine-2-yl)-piperazine-1-yl]-but-2-inyl]-8-aza-spiro [4.5]decane-7,9-dione substantially identical with the continuously measured hydrogen consumption. The addition of the starting material takes 1–2 hours. This means practically that when the addition of the starting material is stopped, the reduction of pressure in the apparatus ceases in a few seconds. The addition takes 1–2 hours, depending on the rate of stirring. The reaction temperature is between 20° C. and 40° C. The reduction having been terminated the catalyst is filtered off. The catalyst can be used directly in the next hydrogenation operations without any further treatment. The filtrate is evaporated the residue suspended in isopropanol and filtered. Thus in the form of white crystals 93.7 g of 8-[4-[4-(pyrimidine-2yl)-piperazine-1-yl]-butyl]-8-aza-spiro-4.5]decane-7,9-dione base are obtained, yield 98.9%. Melting point: 105°–106° C. Content (on the base) 99.9%. According to HPLC analysis the product contains only 0.1% of contaminations.

EXAMPLE 4

Preparation of
8-[4-[4-(pyrimidine-2-yl)-piperazine-1-yl]-butyl]-8-aza-spiro [4.5]decane-7,9-dione A solution of 100 g (0.26 mole) of 8-[4-[4-(pyrimidine-2-yl)-piperazine-1-yl]-but-2-inyl]-8-aza-spiro[4.5]decane-7,9-dione in 50 ml thiophen-free benzene is added to a suspension of 2 g of a palladium/carbon catalyst (palladium content about 5% by weight) and 50 ml of thiophen-free benzene under vigorous stirring at 20°–40° C. under the introduction of hydrogen under a pressure of 1 bar at such a rate that the hydrogen uptake of the unsaturated 8-[4-[4-pyrimidine-2-yl)-piperazine-1-yl]-but-2-inyl]-8-aza-spiro [4.5]decane-7,9-dione added is substantially identical with the calculated hydrogen consumption continuously measured with the aid of a gas burette. This practically means that when the addition of the active ingredient is stopped, the hydrogen consumption ceases within 5–10 seconds. The reaction temperature is 20°–40° C. and the reaction time is 1–4 hours. When the reduction has been terminated, the catalyst is filtered off. The catalyst can be directly used in the next hydrogenating operations without any further treatment. The filtrate is evaporated and the residue is suspended in isopropanol and filtered. Thus in the form of white crystals 100.3 g of 8-[4-[4-(pyrimidine-2yl)-piperazine-1-yl]-butyl]-8-aza-spiro[4.5]decane-7.9-dione base are obtained, yield: about 100%.Mp.:105°–106° C. (according to prior art 90°–98° C.). Content: (on the base) 99.8–100.1%. According to HPLC analysis the product contains only 0.1% of contaminations.

EXAMPLE 5

Preparation of
8-[4-[4-(pyrimidine-2-yl)-piperazine-1-yl]-butyl]-8-aza-spiro[4.5]decane-7,9-dione A solution of 100 g (0.26 mole) of 8-[4-[4-pyrimidine-2-yl)-piperazine-1-yl]-but-2-inyl]-8-aza-spiro[4.5]decane-7,9-dione in 50 ml of tetrahydrofurane is added to a suspension of 1 g of a palladium/carbon catalyst (palladium content about 5% by weight) and 50 ml of tetrahydrofurane under vigorous stirring under the introduction of hydrogen under a pressure of 2 bar at such a rate that the hydrogen uptake of the unsaturated 8-[4-[4-(pyrimidine-2-yl)-piperazine-1-yl]-but-2-inyl]-8-aza-spiro[4.5]decane-7,9-dione added is substantially identical with the calculated hydrogen consumption. This means practically that when the addition of the starting material is stopped, the decrease of the hydrogen pressure in the apparatus ceases within 5–10 seconds. The addition of the starting material takes 1–4 hours, depending on the intensity of stirring. The reaction temperature is adjusted to 15°–30° C. during the complete period of addition. At the end of hydrogenation the catalyst is filtered off. The catalyst can be directly used in the next hydrogenating operations without any further treatment. The filtrate is evaporated, the residue is suspended in isopropanol and filtered. Thus in the form of white crystals 99.7 g of 8-[4-[4-(pyrimidine-2-yl)-piperazine-1-yl]-butyl]-8-aza-spiro[4.5]decane-7,9-dione are obtained, yield 98.7%. Melting point: 105°–106° C. (according to prior art 90°–98° C.). Content (on the base): 99.8–100.1%. According to HPLC analysis the product contains only 0.1% of contaminations.

Example 6

Comparative example

Preparation of
8-[4-[4-(pyrimidine-2-yl)-piperazine-1-yl]-butyl]-8-aza-spiro[4.5]decane-7,9-dione (according to DOS Nr. 3 806 009)

To a solution of 38.15 g (0.1 mole) of 8-[4-[4-(pyrimidine-2-yl)-piperazine-yl1-yl]-but-2-inyl]-8-aza-spiro[4.5]-decane-7,9-dione in 150 ml methanol 1 g of a palladium/carbon catalyst is added. The suspension thus formed is hydrogenated at room temperature under atmospheric pressure and under vigorous stirring until the hydrogen comsumption stops (2 equivalents of hydrogen, about 5.0 liters). The catalyst is filtered off. The catalyst can be directly used in the next hydrogenating operations without a further treatment. The solvent is removed in vacuo.

Thus 36.85 g of 8-[4-[4(pyrimidine-2-yl)-piperazine-1-yl]-butyl]-8-aza-spiro[4.5]decane-7,9-dione are obtained, yield 95.6%. Melting point: 91°–99° C. (according to literature 90°–98° C.). Content (on the base) 102.86%. According to HPLC analysis the product contains the following compounds:
98.33% by weight of the desired compound, i.e. 8-[4-[4-(pyrimidine-2yl)-piperazine-1-yl]-butyl]-8-aza-spiro[4.5]decane-7,9-dione
0.85% by weight of 8-[4-[4-(pyrimidine-2-yl)-piperazine-1-yl]-but-2-enyl]-8-aza-spiro[4.5]decane-7,9-dione,
0.42% by weight of 8-[4-[4-(3,4,5,6-tetrahydropyrimidine-2-yl)-piperazine-1-yl]-butyl]-8-aza-spiro[4.5]decane-7,9-dione,
0.40% by weight of substances of unknown structure.

A product of suitable pharmaceutical purity can only be obtained by recrystallizing the product twice from isopropanol. Yield: 25.9 g (67.2%). Melting point: 105°–106° C. Content (on the base): 99.8–100.0%. According to HPLC analysis the product contains only 0.1% of contaminations.

We claim:
1. Process for the preparation of 8-[4-[4-(pyrimidine-2-yl)-piperazine-1-yl]-butyl]-8-aza-spiro[4.5]decane-7,9-dione (buspiron) of the Formula I

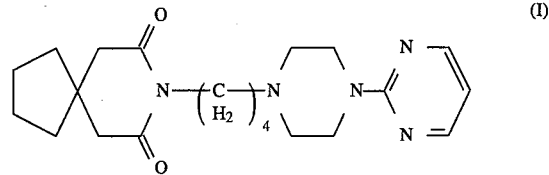

and the hydrochlorides thereof having high purity by subjecting 8-[4-[4-(pyrimidine-2-yl)-piperazine-1-yl]-but-2-inyl]-8-aza-spiro[4.5]decane-7,9-dione of the Formula II

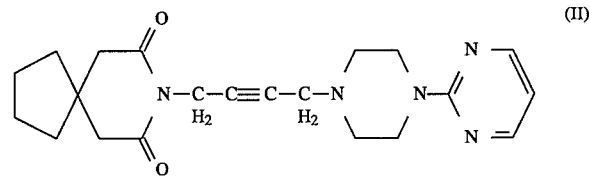

to catalytic hydrogenation in the presence of a palladium or Raney-nickel catalyst in an inert organic solvent and optionally converting the 8-[4-[4-(pyrimidine-2-yl)-piperazine-1-yl]-butyl]-8-aza-spiro[4.5]decane-7,9-dione thus obtained into the hydrochloride thereof which comprises continuously adding a solution of 8-[4-[4-(pyrimidine-2-yl)-piperazine-1-yl]-but-2-inyl]-8-aza-spiro[4.5]decane-7,9-dione formed with an inert organic solvent having a concentration of a least 40% by weight to a suspension of a catalyst in an inert organic solvent, removing the catalyst and subsequently a) isolating the 8-[4-[4-(pyrimidine-2-yl)-piperazine-1-yl]-butyl]-8-aza-spiro[4.5]decane-7,9-dione base, and/or b) treating the 8-[4-[4-(pyrimidine-2-yl)-piperazine-1-yl]-butyl]-8-aza-spiro[4.5]decane-7,9-dione base with hydrogen chloride in ethanol or isopropanol under stirring at a temperature between 15° C. and 40° C. and isolating the 8-[4-[4-(pyrimidine-2-yl)-piperazine-1-yl]-butyl]-8-aza-spiro[4.5]decane-7,9-dione hydrochloride melting at 188°–191° C., or c) treating the 8-[4-[4-(pyrimidine-2-yl)-piperazine-1-yl]-butyl]-8-aza-spiro[4.5]decane-7,9-dione base with hydrogen chloride in ethyl acetate or isopropanol at a temperature not exceeding 70° C. under stirring and isolating the 8-[4-[4-(pyrimidine-2-yl)-piperazine-1-yl]-butyl]-8-aza-spiro[4.5]decane-7,9-dione hydrochloride melting at 201°–203° C.

2. Process according to claim 1 which comprises using a solution of 8-[4-[4-(pyrimidine-2-yl)-piperazine-1-yl]-but-2-inyl]-8-aza-spiro[4.5]decane-7,9-dione of the Formula II having a concentration of 40–70% by weight.

3. Process according to claim 1 which comprises using a solution of 8-[4-[4-(pyrimidine-2-yl)-piperazine-1-yl]-but-2-inyl]-8-aza-spiro[4.5]decane-7,9-dione of the Formula II formed with a polar protic solvent and/or an apolar aprotic solvent and/or a polar aprotic solvent.

4. Process according to claim 1 which comprises using a solution of the compound of the Formula II formed with methanol, ethanol, benzene and/or tetrahydrofurane.

5. Process according to claim 1 which comprises using a suspension of a palladium or Raney-nickel catalyst formed with methanol, ethanol, benzene and/or tetrahydrofurane.

6. Process according to claim 1 which comprises using a palladium catalyst on a support, preferably on carbon.

7. Process according to claim 1 which comprises using the same solvent for dissolving the compound of the formula II as used for suspending the catalyst.

8. Process according to claim 1 which comprises adding the solution of the compound of the Formula II to the suspension of the catalyst at such a rate that the weight ratio of the compound of the Formula II to the catalyst amounts to (0.01–1):1.

9. Process according to claim 1 which comprises treating the base of the Formula I with hydrogen chloride in ethanol or isopropanol in order to prepare 8-[4-[4-(pyrimidine-2-yl)-piperazine-1-yl]-butyl]-8-aza-spiro[4.5]decane-7,9-dione hydrochloride having a melting point of 188°–191° C. at a temperature of about 20° C.

10. Process according to claim 1 which comprises treating the base of the Formula I with hydrogen chloride in ethyl acetate or isopropanol in order to prepare 8-[4-[4-(pyrimidine-2-yl)-piperazine-1-yl]-butyl]-8-aza-spiro[4.5]decane-7,9-dione hydrochloride having a melting point of 201°–203° C. at a temperature between 40° C. and 65° C., preferably at a temperature of about 60° C.

11. Process according to claim 1 which comprises using the base of the Formula I for salt formation in the form of the solution obtained after removing the catalyst.

12. Process according to claim 1 which comprises adding ethanol, isopropanol or ethyl acetate, respectively, containing hydrogen chloride to 8-[4-[4-(pyrimidine-2-yl)-piperazine-1-yl]-butyl]-8-aza-spiro[4.5]decane-7,9-dione base of the Formula I in order to convert the base to 8-[4-[4-(pyrimidine-2-yl)-piperazine-1-yl]-butyl]-8-aza-spiro[4.5]decane-7,9-dione hydrochloride during a period of 5–30 minutes.

13. Process according to claim 1 which comprises stirring the reaction mixture obtained on treating 8-[4-[4-(pyrimidine-2-yl)-piperazine-1-yl]-butyl]-8-aza-spiro[4.5]decane-7,9-dione base of the Formula I with ethanol, isopropanol or ethyl acetate, respectively, containing hydrogen chloride in preparing 8-[4-[4-(pyrimidine-2-yl)-piperazine-1-yl]-butyl] -8-aza-spiro[4.5]decane-7,9-dione hydrochloride during a period of 1–5 hours.

14. Process according to claim 1, wherein said process consists essentially of continuously adding a solution of 8-[4-[4-(pyrimidine-2-yl)-piperazine-1-yl]-but-2-inyl]-8-aza-spiro[4.5]decane-7,9-dione formed with an inert organic solvent having a concentration of at least 40% by weight to a suspension of a catalyst in an inert organic solvent, removing the catalyst and subsequently (a) isolating the 8-[4-[4-(pyrimidine-2-yl)-piperazine-1-yl]-butyl]-8-aza-spiro[4.5]decane-7,9-dione base, and/or (b) treating the 8-[4-[4-(pyrimidine-2-yl)-piperazine-1-yl]-butyl]-8-aza-spiro[4.5]decane-7,9-dione base with hydrogen chloride in ethanol or isopropanol under stirring at a temperature between 15° C. and 40° C. and isolating the 8-[4-[4-(pyrimidine-2-yl)-piperazine-1-yl]-butyl]-8-aza-spiro[4.5]decane-7,9-dione hydrochloride melting at 188°–191° C., or (c) treating the 8-[4-[4-(pyrimidine-2-yl)-piperazine-1-yl]-butyl]-8-aza-spiro[4.5]decane-7,9-dione base with hydrogen chloride in ethyl acetate or isopropanol at a temperature not exceeding 70° C. under stirring and isolating the 8-[4-[4-(pyrimidine-2-yl)-piperazine-1-yl]-butyl]-8-aza-spiro[4.5]decane-7,9-dione hydrochloride melting at 201°–203° C.

15. Process according to claim 1, wherein said process involves no subsequent purification.

16. Process according to claim 1, wherein said process produces 8-[4-[4-(pyrimidine-2-yl)-piperazine-1-yl]-butyl]-8-aza-spiro[4.5]decane-7,9-dione and the hydrochlorides thereof containing impurities of equal to or less than about 0.1% by weight.

* * * * *